US00PP36506P2

(12) United States Plant Patent
Bernuetz

(10) Patent No.: US PP36,506 P2
(45) Date of Patent: Feb. 25, 2025

(54) ***XEROCHRYSUM* PLANT NAMED 'Bonxer 1842'**

(50) Latin Name: *Xerochrysum bracteatum*
Varietal Denomination: Bonxer 1842

(71) Applicant: Andrew Bernuetz, Glenbrook (AU)

(72) Inventor: Andrew Bernuetz, Glenbrook (AU)

(73) Assignee: BONZA BOTANICALS PTY., LTD., Yellow Rock (AU)

( * ) Notice: Subject to any disclaimer, the term of this patent is extended or adjusted under 35 U.S.C. 154(b) by 0 days.

(21) Appl. No.: 18/621,068

(22) Filed: Mar. 28, 2024

(51) Int. Cl.
*A01H 5/02* (2018.01)
*A01H 6/14* (2018.01)

(52) U.S. Cl.
USPC ..... Plt./359

(58) Field of Classification Search
USPC ..... Plt./359
CPC ..... A01H 5/02; A01H 5/00; A01H 6/14
See application file for complete search history.

(56) References Cited

PUBLICATIONS

Four Oaks Trade Show 2023, retrieved on Jul. 24, 2024 at https://www.fouroaks-tradeshow.com/wp-content/uploads/2023/07/Four_Oaks_Trade_Show_Guide_2023.pdf, pp. 1-4, 10, 16, 38, 50, 53. (Year: 2023).*
Granvia 2024 retrieved on Jul. 24, 2024 at https://granvia.eu/product/granvia-white/, 4 pp. (Year: 2024).*
Sparks, California Spring Trials 2023 Preview: White varieties on Display, retrieved on Jul. 24, 2024 at https://granvia.eu/product/granvia-white/, 2 pp. (Year: 2023).*
Vellekoop 2023, Floral Daily California Spring Trials in full swing, retrieved on Jul. 24, 2024 at https://www.floraldaily.com/article/9517105/california-spring-trials-in-full-swing/, 6 pp. (Year: 2023).*

* cited by examiner

*Primary Examiner* — June Hwu
(74) *Attorney, Agent, or Firm* — C. Anne Whealy

(57) ABSTRACT

A new and distinct cultivar of *Xerochrysum* plant named 'Bonxer 1842', characterized by its upright and mounding plant habit; vigorous growth habit; freely flowering habit; semi-double type inflorescences with white-colored involucral bracts; and strong peduncles that hold the inflorescences above and beyond the foliar plane.

2 Drawing Sheets

Figure 1:
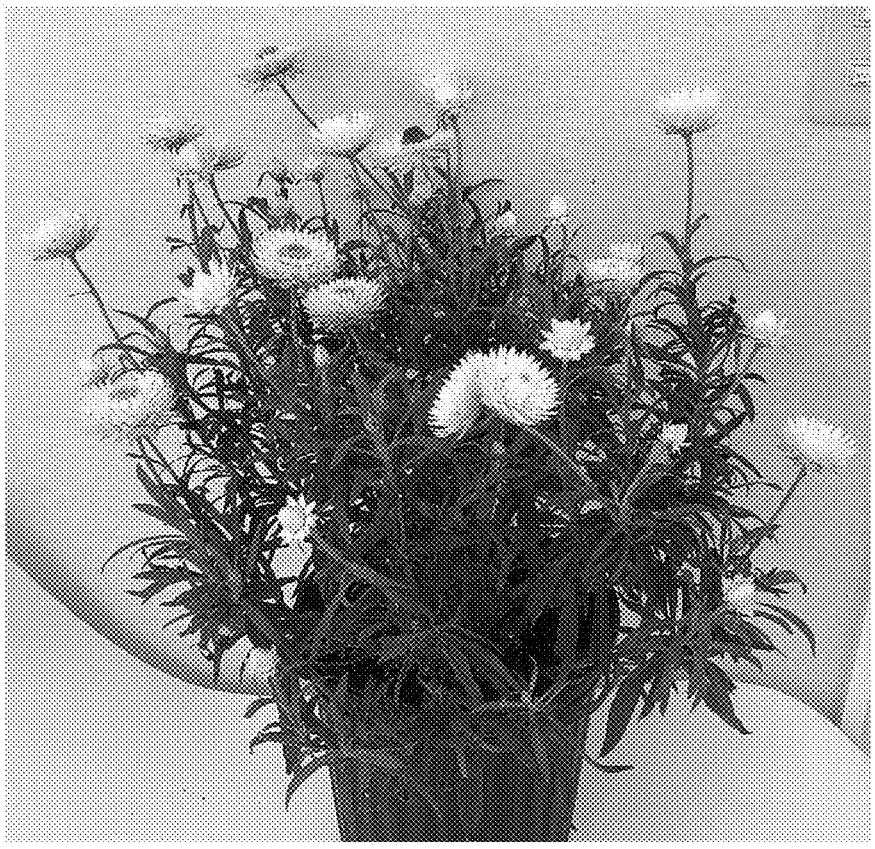

Botanical designation: *Xerochrysum bracteatum.*
Cultivar denomination: 'BONXER 1842'.

STATEMENT REGARDING PRIOR DISCLOSURES BY THE INVENTOR/APPLICANT & ASSIGNEE

The Inventor/Applicant and Assignee, Bonza Botanicals Pty., Ltd. of Yellow Rock, New South Wales, Australia, hereby confirm that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Xerochrysum* plant, botanically known as *Xerochrysum bracteatum*, commonly known as Strawflower, and hereinafter referred to by the name 'Bonxer 1842'.

The new *Xerochrysum* plant is a product of a planned breeding program conducted by the Inventor in Yellow Rock, New South Wales, Australia. The objective of the breeding program is to create and develop new upright *Xerochrysum* cultivars with numerous attractive inflorescences.

The new *Xerochrysum* plant originated from a cross-pollination by the Inventor in July 2017 of a proprietary selection of *Xerochrysum bracteatum* identified as code number 16-75, not patented, as the female, or seed, parent with a proprietary selection of *Xerochrysum bracteatum* identified as code number 16-51, not patented, as the male, or pollen, parent. The new *Xerochrysum* plant was discovered and selected by the Inventor as a single flowering plant within the progeny of the stated cross-pollination in a controlled greenhouse environment in Yellow Rock, New South Wales, Australia in February 2018.

Asexual reproduction of the new *Xerochrysum* plant by terminal cuttings in a controlled greenhouse environment in Yellow Rock, New South Wales, Australia since February 2018 has shown that the unique features of this new *Xerochrysum* plant are stable and reproduced true to type in successive generations.

SUMMARY OF THE INVENTION

Plants of the new *Xerochrysum* have not been observed under all possible combinations of environmental and cultural conditions. The phenotype may vary somewhat with variations in environment such as temperature and light intensity, without, however, any variance in genotype.

The following traits have been repeatedly observed and are determined to be the unique characteristics of 'Bonxer 1842'. These characteristics in combination distinguish 'Bonxer 1842' as a new and distinct *Xerochrysum* plant:

1. Upright and mounding plant habit.
2. Vigorous growth habit.
3. Freely flowering habit.
4. Semi-double type inflorescences with white-colored involucral bracts.
5. Strong peduncles that hold the inflorescences above and beyond the foliar plane.

In side-by-side comparisons, plants of the new *Xerochrysum* differ primarily from plants of the female parent selection in involucral bract color as inflorescences of plants of the new *Xerochrysum* have white-colored involucral bracts whereas inflorescences of plants of the female parent selection have lemon yellow-colored involucral bracts.

In side-by-side comparisons, plants of the new *Xerochrysum* differ primarily from plants of the male parent selection in involucral bract color as inflorescences of plants of the new *Xerochrysum* have white-colored involucral bracts whereas inflorescences of plants of the male parent selection have orange-colored involucral bracts.

Plants of the new *Xerochrysum* can be compared to plants of the *Bracteantha bracteata* 'Bonxero 148', disclosed in U.S. Plant Pat. No. 30,398. In side-by-side comparisons, plants of the new *Xerochrysum* differ primarily from plants of 'Bonxero 148' in the following characteristics:

1. Plants of the new *Xerochrysum* are more freely branching than plants of 'Bonxero 148'.
2. Plants of the new *Xerochrysum* have smaller and lighter green-colored leaves than plants of 'Bonxero 148'.
3. Plants of the new *Xerochrysum* are more freely flowering than plants of 'Bonxero 148'.
4. Inflorescences of plants of the new *Xerochrysum* are more incurved than and not as flat as inflorescences of plants of 'Bonxero 148'.
5. Inflorescences of plants of the new *Xerochrysum* have white-colored involucral bracts whereas inflorescences of plants of 'Bonxero 148' have bright yellow-colored involucral bracts.
6. Plants of the new *Xerochrysum* have shorter peduncles than plants of 'Bonxero 148'.

BRIEF DESCRIPTION OF THE PHOTOGRAPHS

The accompanying photographs illustrate the overall appearance of the new *Xerochrysum* plant. These photographs show the colors as true as it is reasonably possible to obtain in colored reproductions of this type. Colors in the photographs may differ slightly from the color values cited in the detailed botanical description which accurately describe the colors of the new *Xerochrysum* plant.

The photograph on the first sheet (FIG. 1) is a side perspective view of a typical flowering plant of 'Bonxer 1842' grown in a container.

Figure 2:
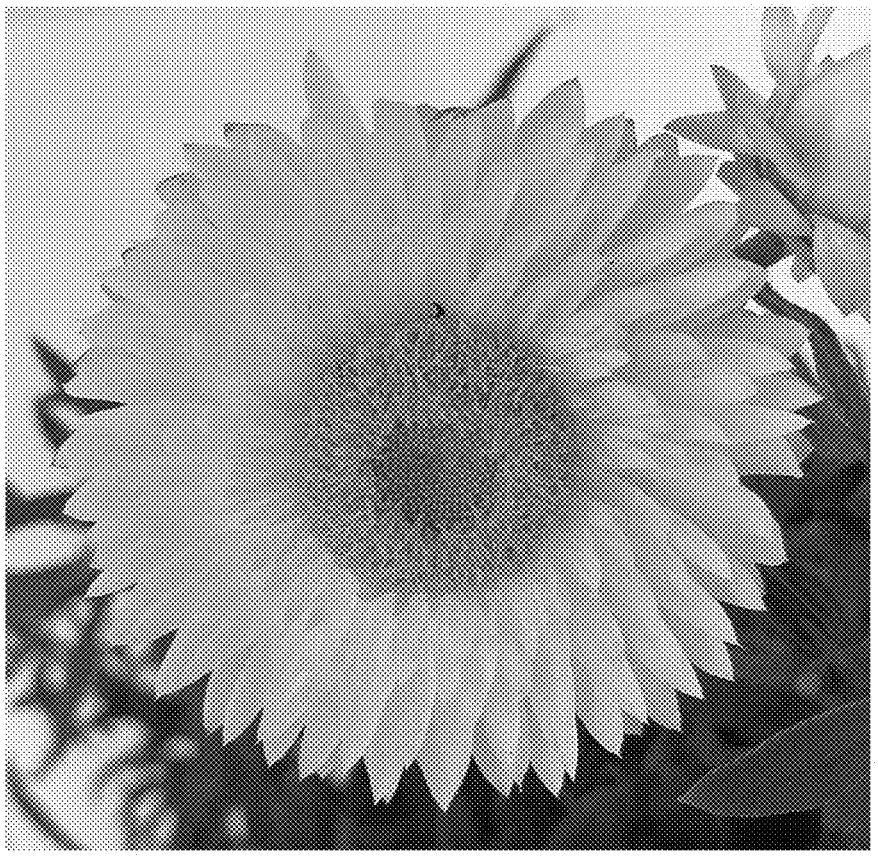

The photograph on the second sheet (FIG. 2) is a close-up view of a typical inflorescence of 'Bonxer 1842'.

DETAILED BOTANICAL DESCRIPTION

The aforementioned photographs and following observations and measurements describe plants grown during the summer in 24-cm containers in an outdoor nursery in Higashiomi, Shiga, Japan and under conditions and practices which approximate those generally used in commercial *Xerochrysum* production. During the production of the plants, day temperatures averaged 23° C. and night averaged 13° C. Measurements and numerical values represent averages for typical flowering plants. Plants were four months old when the photographs were taken and five months old when the detailed description was taken. In the following description, color references are made to The Royal Horticultural Society Colour Chart, 2015 Edition, except where general terms of ordinary dictionary significance are used.

Botanical classification: *Xerochrysum bracteatum* 'Bonxer 1842'.

Parentage:

*Female, or seed, parent*.—Proprietary selection of *Xerochrysum bracteatum* identified as code number 16-75, not patented.

*Male, or pollen, parent*.—Proprietary selection of *Xerochrysum bracteatum* identified as code number 16-51, not patented.

Propagation:

*Type*.—Terminal vegetative cuttings.

*Time to initiate roots, summer*.—About seven days at temperatures about 18° C. to 21° C.

*Time to initiate roots, winter*.—About ten days at temperatures about 18° C. to 21° C.

*Time to produce a rooted cutting, summer*.—About three weeks at temperatures about 18° C. to 21° C.

*Time to produce a rooted cutting, winter*.—About four weeks at temperatures about 18° C. to 21° C.

*Root description*.—Fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant form and growth habit*.—Annual plant; upright and mounding plant habit with inflorescences held above the foliage on strong peduncles; vigorous growth habit.

Plant height.—About 45 cm.

Plant diameter or spread.—About 47 cm.

*Lateral branches*.—Quantity per plant: Freely branching habit with about twelve primary lateral branches with numerous secondary lateral branches developing per plant. Length: About 31 cm. Diameter: About 4.6 mm. Internode length: About 1.7 cm. Aspect: Mostly upright to slightly outwardly. Strength: Strong. Texture: Moderately pubescent. Color: Close to 138B.

*Leaf description*.—Arrangement: Alternate, simple; sessile. Length: About 6.2 cm. Width: About 8 mm. Shape: Linear. Apex: Acuminate. Base: Attenuate. Margin: Entire; not undulate to slightly undulate. Texture, upper and lower surfaces: Rough, moderately pubescent. Venation pattern: Pinnate; reticulate. Color: Developing and fully expanded leaves, upper surface: Close to 138A; venation, close to 144C. Developing and fully expanded leaves, lower surface: Close to 138B; venation, close to 144C.

*Inflorescence description*.—Appearance: Terminal semi-double type inflorescence form with numerous deltoid involucral bracts; inflorescences concave in cross-section; involucral bracts and disc florets developing acropetally on a capitulum; inflorescences positioned above the foliar plane on strong peduncles; inflorescences face mostly upright. Flowering habit: Freely flowering habit; about 55 inflorescence buds and inflorescences per plant. Fragrance: None detected. Time to flower: In Japan, plants begin to flower about 21 weeks after planting and in the garden, plants flower continuously from the spring until late autumn. Post-production longevity: Inflorescences maintain good substance for about seven to ten days on the plant; inflorescences persistent.

*Inflorescence buds*.—Height: About 1.8 cm. Diameter: About 1.4 cm. Shape: Ovoid with acute apex. Color: Close to 155B.

*Inflorescence size*.—Diameter: About 5.5 cm. Depth (height): About 2.1 cm. Disc diameter: About 1.7 cm. Disc height: About 7.1 mm.

*Receptacles*.—Diameter: About 2.3 cm. Height: About 7.2 mm. Color: Close to 145D.

*Involucral bracts*.—Quantity per inflorescence and arrangement: About 324 arranged in numerous whorls; bracts imbricate. Length: About 2 cm. Width: About 6 mm. Shape: Deltoid. Apex: Acuminate. Base: Truncate. Margin: Entire. Texture, upper and lower surfaces: Smooth, glabrous; papery; durable. Orientation: Initially upright becoming more outward with development. Color: When opening and fully opened, upper surface: Close to 155B; color does not change with subsequent development. When opening and fully opened, lower surface: Close to 155B; color does not change with subsequent development.

*Disc florets*.—Quantity per inflorescence and arrangement: Numerous disc florets are spirally arranged in the center of the receptacle. Length: About 1 cm. Diameter, distally: About 1.5 mm. Diameter, proximally: About 0.8 mm. Shape: Tubular; apex dentate, five-pointed. Texture, inner and outer surfaces: Smooth, glabrous. Color: Apex: Close to 14A. Midsection and base: Close to 145D.

*Peduncles*.—Length: About 5.6 cm. Diameter: About 2.8 mm. Strength: Strong. Aspect: Mostly upright. Texture: Rough, pubescent. Color: Close to 138B.

*Reproductive organs*.—Androecium: Quantity per disc floret: About five. Filament length: About 2.6 mm. Filament color: Close to 157D. Anther size: About 1 mm by 2.5 mm. Anther shape: Linear. Anther color: Close to 14A. Pollen amount: None observed. Gynoecium: Quantity per disc floret: One. Pistil length: About 8.3 mm. Stigma shape: Bi-parted. Stigma color: Close to 14B. Style color: Close to 157D. Ovary color: Close to 155A.

*Seeds and fruits*.—To date, seed and fruit production has not been observed on plants of the new *Xerochrysum*.

Pathogen & pest resistance: To date, plants of the new *Xerochrysum* have not been observed to be resistant to pathogens and pests common to *Xerochrysum* plants.

Temperature tolerance: Plants of the new *Xerochrysum* have been observed to tolerate temperatures ranging from about 1° C. to about 35° C.

It is claimed:

1. A new and distinct *Xerochrysum* plant named 'Bonxer 1842' as herein illustrated and described.

* * * * *